United States Patent [19]
Green et al.

[11] Patent Number: 5,944,735
[45] Date of Patent: Aug. 31, 1999

[54] PROCESS FOR STENT COMPRESSION

[75] Inventors: Nicholas A. Green, Kinnelon, N.J.; Fred E. Williams, Jr., Arab, Ala.

[73] Assignees: Atrion Medical Products, Inc., Arab, Ala.; Cordis Corporation, Miami, Fla.

[21] Appl. No.: 08/961,287

[22] Filed: Oct. 30, 1997

Related U.S. Application Data

[60] Division of application No. 08/745,317, Nov. 12, 1996, Pat. No. 5,746,764, which is a continuation-in-part of application No. 08/567,136, Dec. 4, 1995, abandoned.

[51] Int. Cl.⁶ .................................................. A61M 29/00
[52] U.S. Cl. ........................... 606/194; 606/108; 128/898
[58] Field of Search ................... 606/194–198, 606/108; 604/96; 623/1, 12; 128/898

[56] References Cited

U.S. PATENT DOCUMENTS

| | | | |
|---|---|---|---|
| 5,378,237 | 1/1995 | Boussignac et al. | |
| 5,437,083 | 8/1995 | Williams et al. | |
| 5,456,694 | 10/1995 | Marin et al. | 606/194 |
| 5,484,449 | 1/1996 | Amundson et al. | |
| 5,546,646 | 8/1996 | Williams et al. | |
| 5,593,412 | 1/1997 | Martinez et al. | 606/194 |
| 5,628,754 | 5/1997 | Shevlin et al. | 606/108 |
| 5,693,085 | 12/1997 | Buirge et al. | 606/192 |
| 5,738,674 | 4/1998 | Williams et al. | |

FOREIGN PATENT DOCUMENTS 0630623 12/1984 European Pat. Off.

*Primary Examiner*—Michael Buiz
*Assistant Examiner*—Kevin Truong
*Attorney, Agent, or Firm*—Trexler, Bushnell, Giangiorgi & Blackstone, Ltd.

[57] ABSTRACT

In accordance with the present invention, a fluid compression instrument and method for particular use in pre-surgically securing and conforming a vascular stent upon an angioplasty balloon, includes a housing for containing pressurized fluid and an elastic enclosing diaphragm secured within the housing and having an internal cavity and opening arranged to receive the stent disposed on the balloon catheter for secured compression. A pressure chamber is arranged within the housing as an envelope about the diaphragm to enable pressurized fluid forces within the pressure chamber to be imposed upon the outer surface of the diaphragm and transmitted through the diaphragm enabling circumferential application against the inserted stent in order uniformly to compress the stent with correspondingly secured purchase against the deflated balloon surface, producing complete adhesion of the stent thereon. The subsequent balloon inflation angioplasty and stent expansion is not impaired since the balloon remains in its deflated shape with the compressed stent closely conforming in contour throughout the balloon's 360° periphery. The entire stent mesh is uniformly compressed down including the open stent ends which prevents the many tiny stent mesh edges from protruding out and effectively prevents both vascular abrasion as well as shifting of the stent on the deflated balloon during the angioplasty insertion procedure.

5 Claims, 5 Drawing Sheets

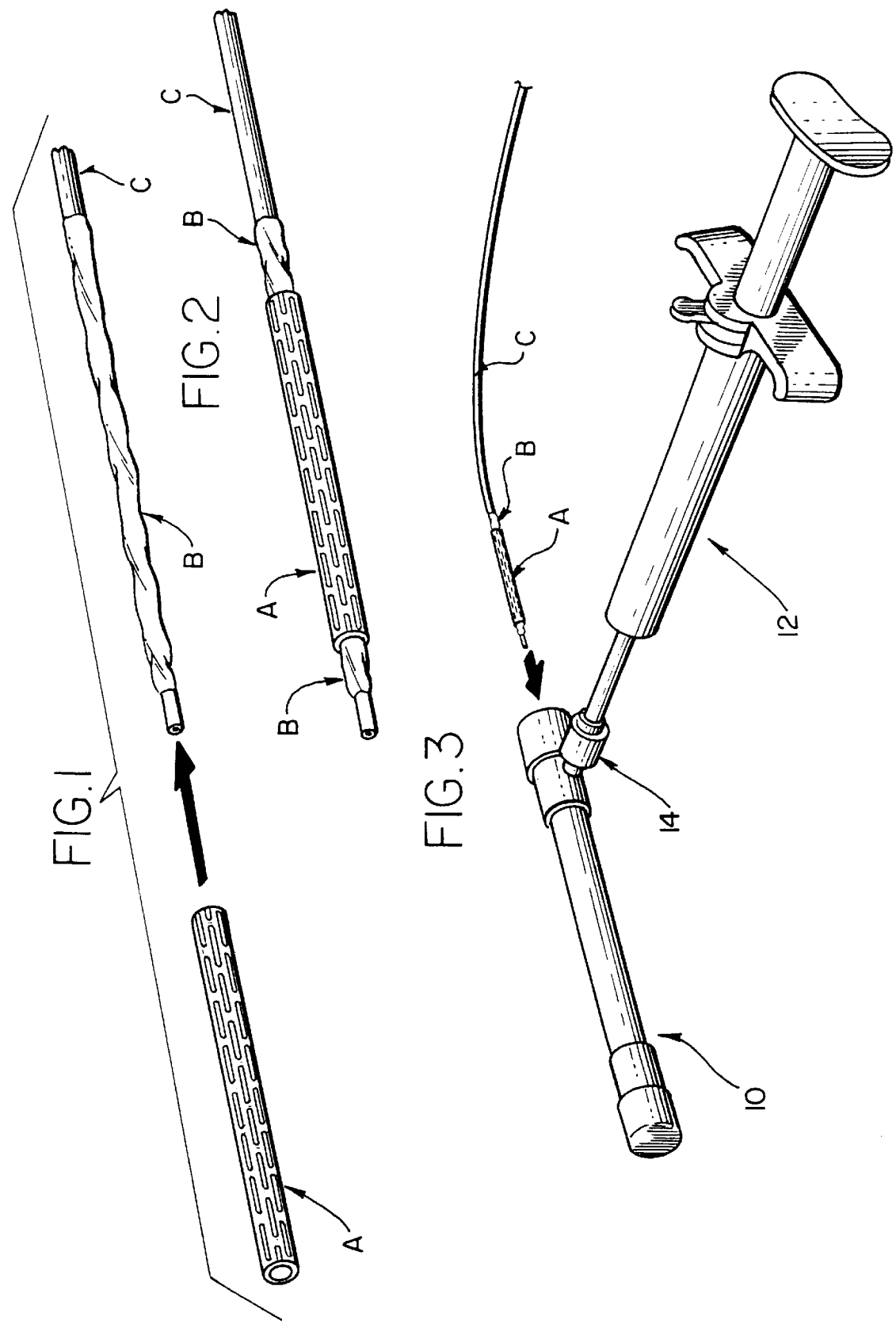

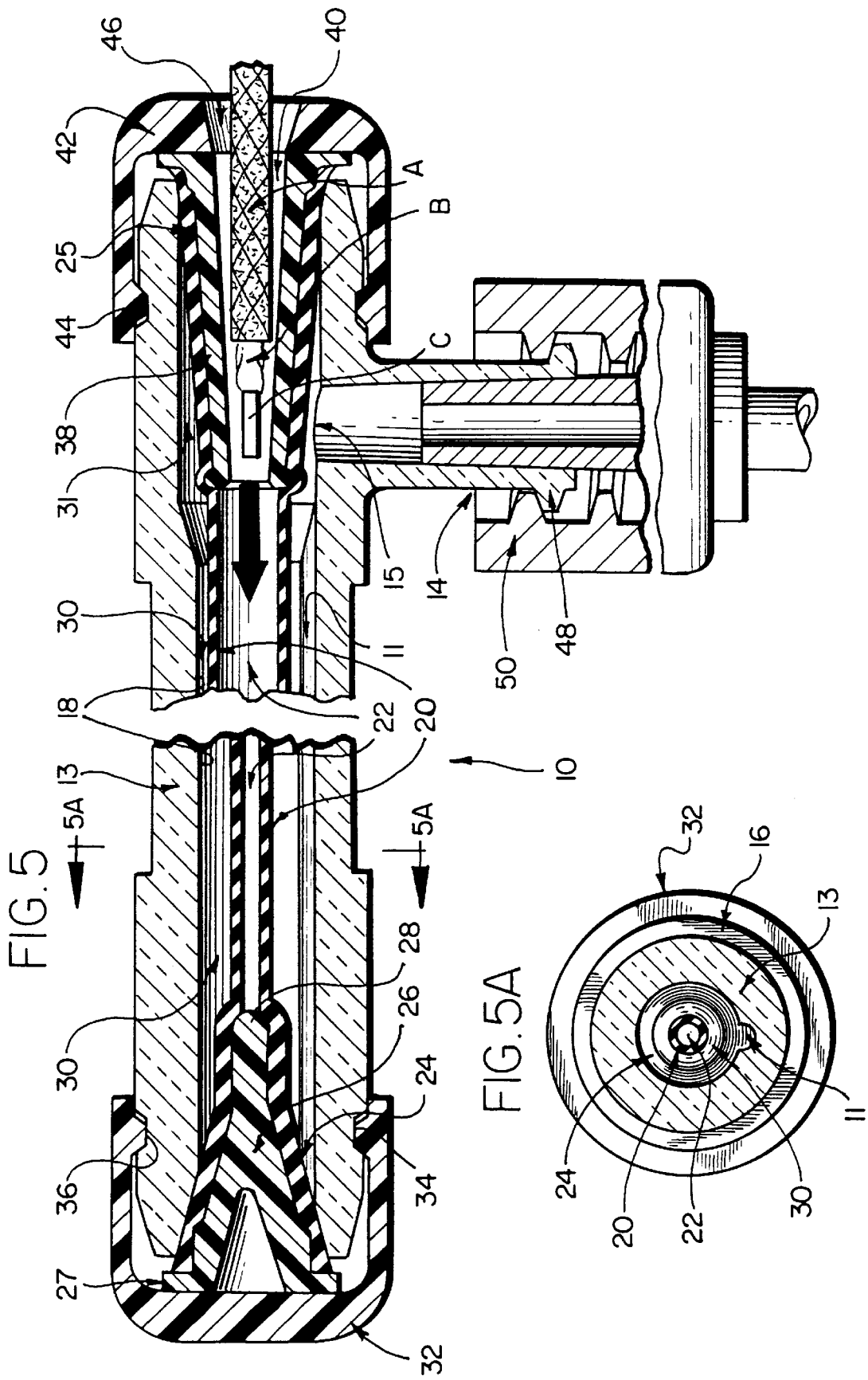

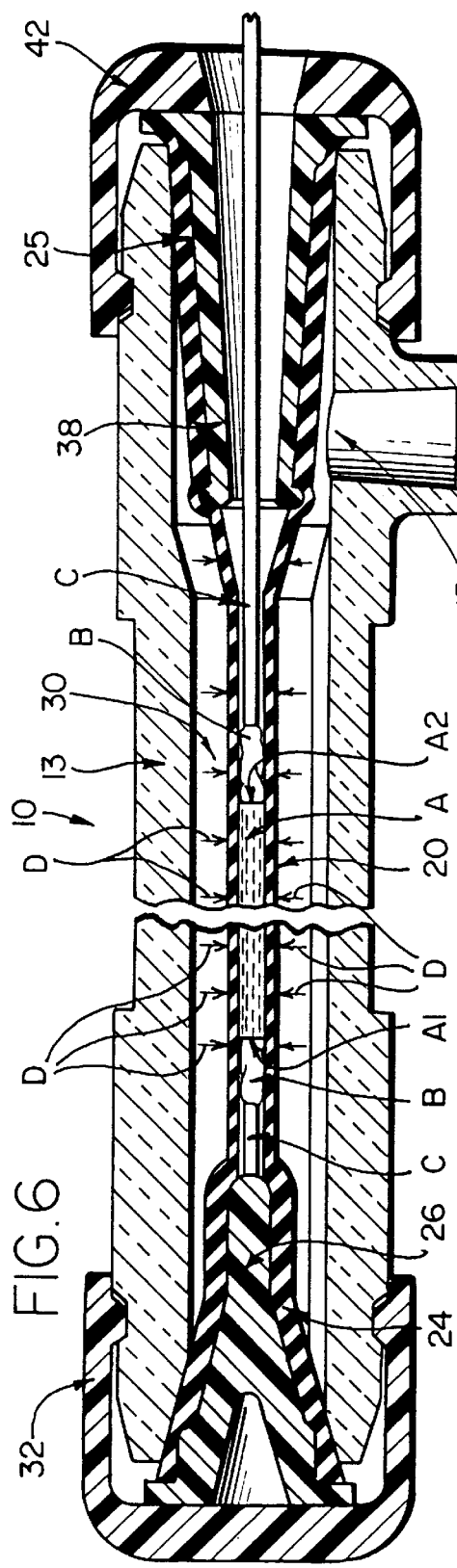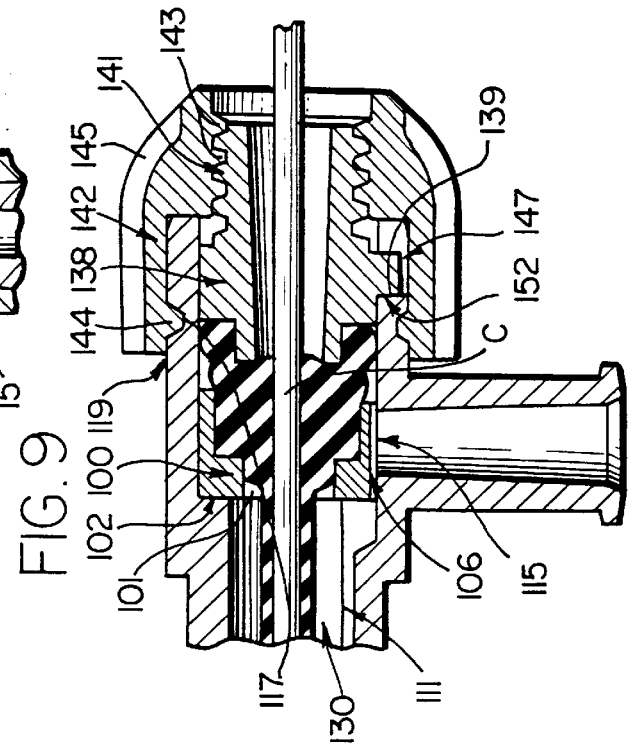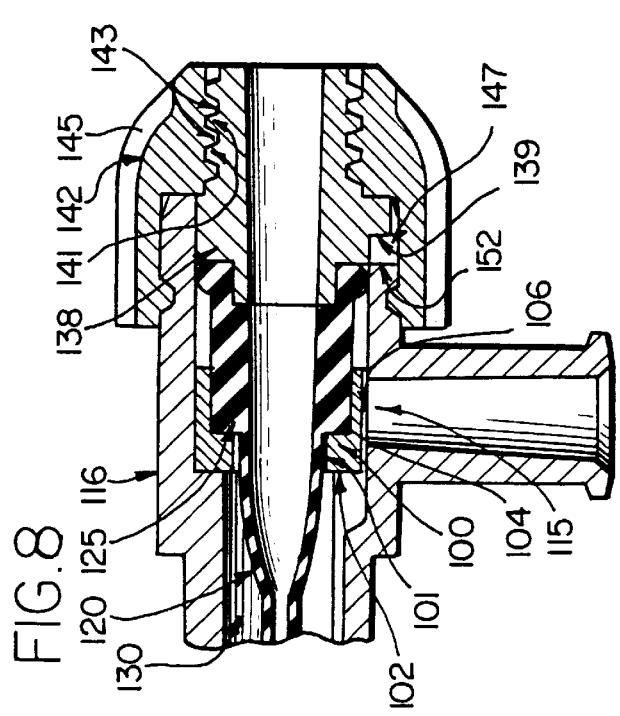

PROCESS FOR STENT COMPRESSION

CROSS REFERENCE TO RELATED APPLICATION

This is a divisional application of copending application Ser. No. 08/745,317 filed on Nov. 12, 1996 now U.S. Pat. No. 5,746,764 which was a continuation-in-part application of Ser. No. 08/567,136 filed on Dec. 4, 1995, now abandoned.

BACKGROUND OF THE INVENTION

The present invention relates to surgical angioplasty balloon procedures and more particularly relates to fluid compression instruments for particular use in pre-surgical securement of an angioplasty stent onto a balloon catheter for subsequent implantation of the stent in an angioplasty procedure.

In order to improve the effectiveness of vascular angioplasty in relieving blockage or repairing cardiovascular damage, a stainless steel mesh stent of tubular configuration has been developed for vascular implantation. The stent is introduced by a balloon catheter on which the stent is inserted and expanded against the vascular implantation site. Precisely locating, implanting and expanding the stent requires that it be securely carried on the balloon catheter for both transport to the implantation site and expansion by the balloon. Mechanical crimping of the stent onto the catheterized balloon is currently employed for the securement to the balloon. Mechanical crimping is effected by opening and closing jaws of the crimping tool, but cannot produce 360° circumferential uniformity in compression and conforming purchase of the stent to the deflated balloon surface. As such, there is a danger of potential slippage of the stent on the deflated balloon before or during an angioplasty procedure for vascular implant of the stent. Also, there is the possibility that the stent will not be uniformly and evenly expanded by the balloon catheter during expansion thereof. Moreover, any mesh material of the stent which is not completely crimped can lead to abrasion and damage to the vascular tissue during the stent insertion and implantation angioplasty procedure. These and other disadvantages are eliminated by the instruments and method in accordance with the present invention.

SUMMARY OF THE INVENTION

In accordance with the present invention, a fluid compression instrument and method for particular use in pre-surgically securing and conforming a vascular stent upon an angioplasty balloon, includes a housing for containing pressurized fluid and an elastic enclosing diaphragm secured within the housing and having an internal cavity and opening arranged to receive the stent disposed on the balloon catheter for secured compression. A pressure chamber is arranged within the housing as an envelope about the diaphragm to enable pressurized fluid forces within the pressure chamber to be imposed upon the outer surface of the diaphragm and transmitted through the diaphragn enabling circumferential application against the inserted stent in order uniformly to compress the stent with correspondingly secured purchase against the deflated balloon surface, producing complete adhesion of the stent thereon. The subsequent balloon inflation angioplasty and stent expansion is not impaired since the balloon remains in its deflated shape with the compressed stent closely conforming in contour throughout the balloon's 360° periphery. The entire stent mesh is uniformly compressed down including the open stent ends which prevents the many tiny stent mesh edges from protruding out and effectively prevents both vascular abrasion as well as shifting of the stent on the deflated balloon during the angioplasty insertion procedure.

In one embodiment, the housing and the enclosing diaphragm have tubular configurations with an annular pressure chamber defined between the tubular housing wall and the tubular elastic diaphragm. The ends of the tubular diaphragm are sealed to the housing wall forming the ends of the pressure chamber. One end of the housing and diaphragm seal has an access passageway for insertion and withdrawal of the balloon catheter carrying the stent into the diaphragm lumen. Hydraulic or pneumatic fluid pressurization of the compression chamber and evacuation are provided by a syringe-type fluid control instrument coupled to a conduit through the housing. In the preferred, illustrated embodiment, the pressurization of the diaphragm is attained with a fluid medium such as air or a liquid, such as sterile saline. It is envisioned, however, that other media capable of transmitting pressure uniformly may be developed and utilized as an equivalent to fluid medium discussed hereinafter.

BRIEF DESCRIPTION OF THE DRAWINGS

FIG. 1 is a perspective view of vascular stent device disengaged from an angioplasty balloon catheter device;

FIG. 2 is an assembled view of the stent mounted on the balloon catheter shown in FIG. 1;

FIG. 3 is a perspective view of one embodiment of the fluid compression instrument in accordance with the present invention, which is coupled to a fluid supply syringe and further shows the assembled stent upon the balloon catheter of FIG. 2 preparatory to insertion into the fluid compression instrument;

FIG. 5 is a sectional view of the assembled fluid compression instrument of FIGS. 3 and 4 which has been fragmented into two longitudinal portions for comparison of both normal atmospheric pressure condition and partial evacuation conditions within the instrument;

FIG. 5A is a sectional view taken along a plane indicated by line 5A—5A in FIG. 5;

FIG. 6 is a sectional view similar to FIG. 5 showing fluid pressurization condition within the instrument and the compressed condition of an inserted stent uniformly compressed into conforming securement onto the balloon catheter;

FIG. 8 is a fragmentary, sectional view showing a portion of a second embodiment of a fluid compression instrument according to the invention, showing a movable seal assembly therein; and FIG. 9 is a view similar to FIG. 8 showing the sealed condition of the movable seal assembly in which an inserted catheter tube is supported during high pressure, compression operation of the instrument.

DETAILED DESCRIPTION OF THE ILLUSTRATED EMBODIMENT

Figure 4:
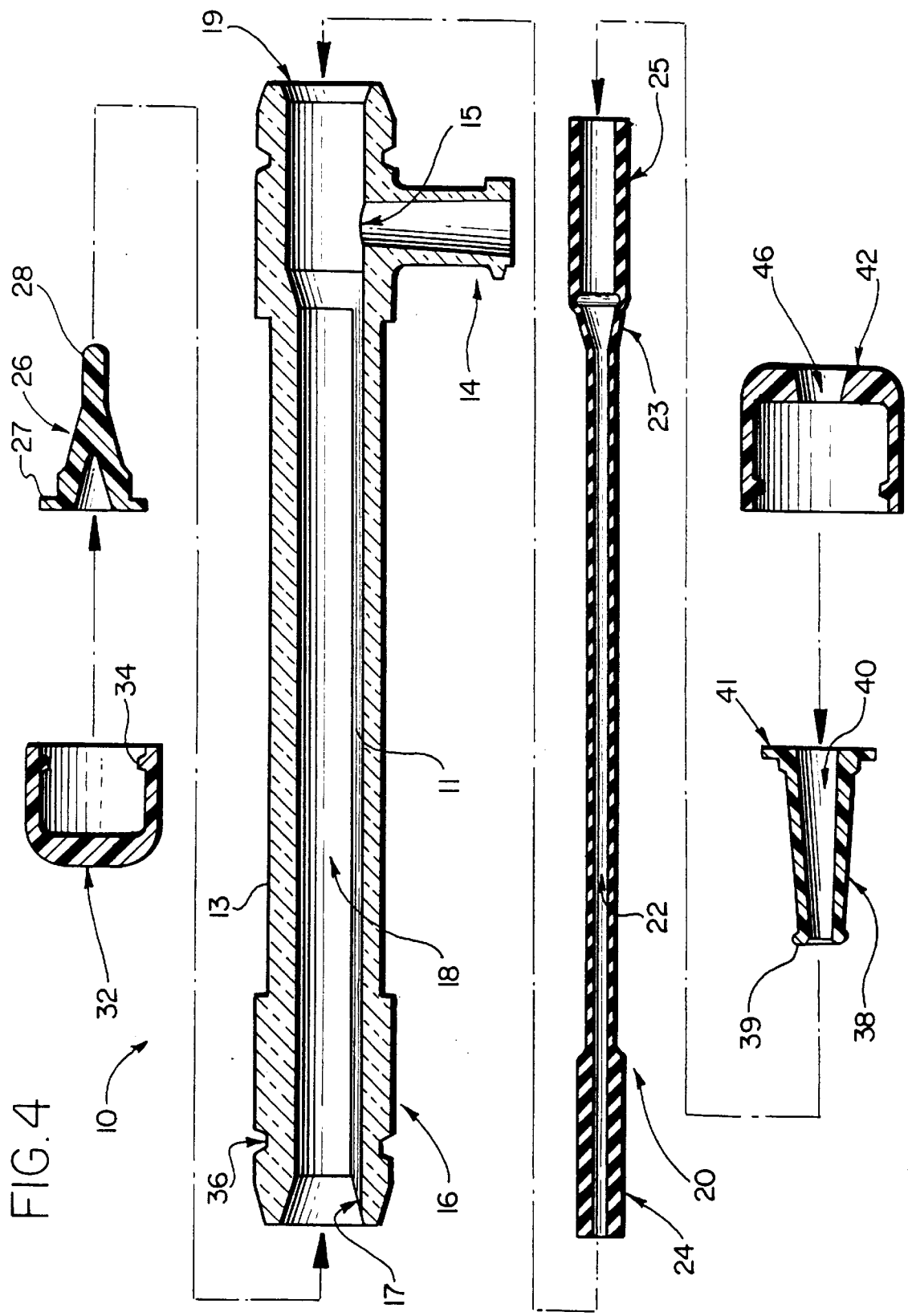
FIG. 4 is an exploded sectional view of the fluid compression instrument shown in FIG. 3.

Referring to FIGS. 1 and 2, a balloon-expandable "stent" A having a conventional, stainless steel, slotted tubular mesh configuration is shown in an unexpanded or intermediate condition. The stent A is slipped onto a deflated angioplasty balloon B and catheter C unit, the stent A being held on the balloon initially in simple frictional fit. In accordance with the present invention, the frictional fit and the conformity of the stent A to the deflated balloon B with uniform cohesive purchase therebetween are improved by a fluid compression instrument illustrated in one embodiment generally designated by a reference character 10 shown in FIG. 3. A fluid pressurization syringe 12 is coupled at 14 to the instrument housing 16 and employed for both pressurizing and depressurizing the operating fluid, typically a saline solution within the compression instrument 10, as more fully described hereinafter. A preferred syringe instrument of the type employed in angioplasty balloon inflation features a quick release mechanism which allows precise control of both initial and final fluid pressurization is described for example in U.S. Pat. No. 5,168,757.

As shown in FIG. 3, the stent A slipped over the balloon B are together inserted into the compression instrument 10 wherein the circumferentially uniform compression of the stent produces the corresponding uniformly cohesive purchase of the stent onto the deflated balloon. Thereafter, the compressed stent and balloon are removed from the compression instrument 10 and are then ready for a surgical angioplasty implantation wherein the uniformly compressed stent on the deflated balloon enables precise location of the implanted stent in the vascular implantation site.

Referring now to FIGS. 4 and 5, the compression instrument 10 includes an elongate, tubular main housing body 16, with an internal, elongate vent or pressure distribution groove 11 formed therein. The tubular housing 16 is molded to withstand internal pressures of 450 psi or greater during the stent compression operation. A tubular, elastic diaphragm generally designated 20 is mounted within the housing bore 18.

The tubular diaphragm 20 is molded from elastomer capable of withstanding a 450 psi or greater pressure externally applied for transmission to the stent A inserted within the diaphragm lumen 22 during the stent compression operation. The diaphragm 20 has an enlarged annular wall 24 at one end having an opening which is sealed by an inserted ferrule plug 26. The ferrule plug 26 has a generally cone-shaped configuration with a closed, projecting apex 28. The annular diaphragm endwall 24 is stretched over the ferrule plug 26 and clamped between the internally projecting ferrule plug and the tapering housing rim portion 17 to close and seal one end of an elongate, annular pressure chamber 30 formed between the internal housing bore wall 18 and the tubular wall of the diaphragm 20. In the illustrated embodiment, a housing cap 32 is snap fit at bead 34 into a peripheral housing groove 36 to maintain end clamping by the cap 32 against an end flange 27 formed on a ferrule plug 26 and sealing clamp of the ferrule plug 26 against the diaphragm wall portion 24. The initial or unexpanded internal diameter of the lumen 22 is slightly less than the desired final diameter of the stent A, once compressed onto the balloon catheter B.

Figure 7:
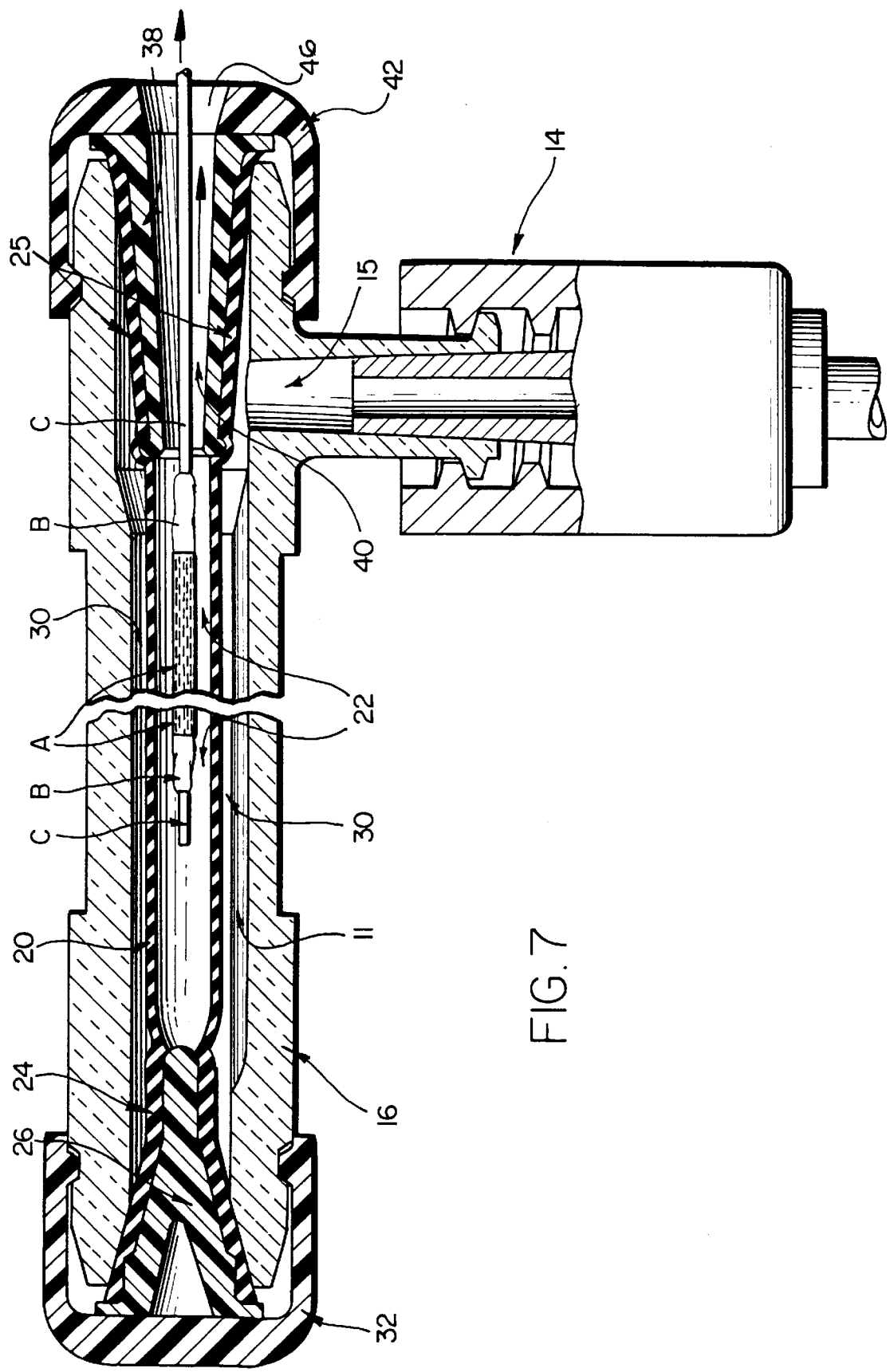
FIG. 7 is a sectional view similar to FIG. 6 showing an evacuation condition within the instrument following the compression condition of FIG. 6, and withdrawal of the compressed stent/balloon assembly following the compression operation of the instrument.

At the opposite, open end 19 of the housing 16, the tubular diaphragm 20 has an enlarged annular endwall 25 into which an open or through passageway ferrule generally designated 38 is inserted to clamp the annular diaphragm wall 25 against the rim of the housing opening 19 which seals the adjacent end 31 of the pressure chamber 30. The passageway ferrule 38 has a through bore 40 which provides an access passageway for insertion of the uncompressed stent A on the balloon B into the lumen 22 of the tubular diaphragm 20 as shown in FIG. 5. The end cap 42 is snap fit at 44 to the housing to maintain end clamping against an end flange 41 formed on the ferrule 38 and sealing clamp of the diaphragm wall 25. The cap 42 also has a through passageway 46 aligned with the ferrule passageway 40 providing access passageway for the insertion and withdrawal of the stentf-balloon as shown in FIGS. 5 and 7.

Referring again to FIG. 4, the fluid coupling 14 of the housing 16 provides a through port 15 which communicates with the annular pressure chamber 30 for both pressurization and evacuation of the pressure chamber 30 by the coupled syringe 12. The elongate inward taper of the passageway ferrule 38 extends longitudinally beyond the transverse opening of the coupling port 15 in order to annularly support the diaphragm wall 25 and thus prevent any induced deflection of the wall 25 which could otherwise be drawn against the opening of the port 15 by suction action of the evacuation pressure reduced by the action of the syringe 12 in operation as more fully described hereinafter.

Additionally, the raised ring forming an inlet 39 on the passageway ferrule 38 promotes slight stretching of the annular diaphragm wall 25 and facilitates expansion of the diaphragm 22 during the evacuation of the compression chamber 30 by the syringe action. The tapered diaphragm portion 23 leading to the endwall portion 25 helps to prevent the tubular diaphragm from extruding between the stent/balloon A, B and the interior surface of the passageway ferrule 38 and eliminate a rupturing hazard during pressurizing operations.

In operation to compress a stent A in uniform securement onto the deflated balloon B, the fluid syringe 12 (FIG. 3) is connected to the coupler 14 for example by respective luer couplings 48 and 50 in the embodiment shown in FIG. 5. In a preparatory priming step, the syringe 12 first delivers pressurized fluid such as distilled water or saline solution, through the port 15 to fill the annular pressure chamber 30 after which the inflator plunger is retracted until all air voids have been purged. Thereafter, using the syringe 12, the pressure chamber 30 is partially evacuated to cause the tubular diaphragm to expand radially the lumen 22 as shown in the righthand portion of the instrument 10 shown in FIG. 5. The lefthand portion of FIG. 5 illustrates the normal or unpressurized diameter of the lumen 22. The vent groove 11 prevents fluid flow blockage due to any collapse of the diaphragm 20 against the housing bore wall 18 during the evacuating operation. The resulting dilation of the lumen 22 allows expanded clearance for insertion of the stent/catheter-balloon A, B to be inserted through the open, thorough passageway 40 as shown in FIG. 5 and entirely through lumen 22 until the leading or nose portion of the catheter C engages the projecting ferrule apex 28 at the closed end of the lumen 22. In order to view the insertion and passage of the stent/balloon/catheter A, B, C through the lumen 22, the diaphragm 20 is preferably transparent and appropriately molded, for example from silicone elastomer. Correspondingly, the housing wall 18 is transparent, and to improve visibility the housing wall has a medial, reduced diameter portion 13 for viewing the progressive passage of the catheter tip C and stent A through the diaphragm lumen 22.

After fully inserting the uncompressed stent A/balloon B the syringe 12 again pressurizes the pressure chamber 30 to a pressure for example 300 psi to 450 psi resulting in a circumferentially and longitudinally uniform compression of the tubular diaphragm 20 which transmits the hydraulic pressure in the correspondingly uniform longitudinal distribution of circumferential compressive forces indicated by arrows D along the entire length of the stent A. The uniformly distributed compression forces result in a compression of the annular mesh wall of the stent from an original, uncompressed outer diameter of, for example, 0.056 inch reduced to the compressed outer diameter approximately 0.050 inch using a diaphragm tube of normal, uncompressed diameter approximately 0.046 inch. Most importantly, the uniform longitudinal and radial compression transmitted by the tubular diaphragm 20 results in corresponding compression force distribution on the stent to enable the compressed mesh of the stent to closely conform to the surface of the deflated balloon with maximum adhesive purchase therebetween, without any exposure to hazard of damage from localized overcompression of the stent, which has occurred in prior methods of mechanically crimping the stent. Moreover, the uniformly compressed stent A achieves improved purchase and grip onto the balloon B to prevent any premature displacement of the stent along the balloon during subsequent surgical angioplasty procedures for coronary or vascular implantation of the stent. Additionally, the mesh body of the stent and most importantly, the open ends of the stent, A1 and A2, are uniformly compressed down against the balloon as shown in FIG. 6 to prevent possibility of lead or intermediate edges of the stent catching against the vascular wall to cause damaging abrasion, thus flirter improving surgical safety.

Since the mesh stent is readily compressed under the uniform hydraulic pressure imposed by the compression chamber 30, the compressed stent conforms to the deflated balloon shape in seconds and is ready to be withdrawn from the instrument 10 facilitated by again retracting the syringe 12 plunger to evacuate the compression chamber 30 and re-dilate the tubular diaphragm 20 as shown in FIG. 7. Thereafter, the compressed stentfballoon/catheter A, B, C is retracted from the tubular lumen 22 and removed from the instrument 10, ready for subsequent angioplasty procedure.

Referring now to FIGS. 8 and 9, a second embodiment 110 of the fluid compression instrument in accordance with the present invention is shown, in which a thickened endwall portion 125 of the tubular diaphragm 120 is squeezed down to grasp and support the portion of the catheter tube C as shown in FIG. 9, extending through the open end 119 of the housing 116 from the inserted stent/balloon portions (not shown). The squeezed diaphragm wall portion 125 also forms a compression flange which withstands highly pressurized fluid, for example, 450 psi or higher, and the grip of the catheter extension C prevents its movement during the higher pressurization as shown in FIG. 9. The compression flange portion 125 is squeezed radially by longitudinal compression against an annular seat member 100 which fits against an internal shoulder 102 of a housing wall 116. The seat 100 also has an internal shoulder 104 against which the compression flange portion 125 is compressed by longitudinal force imposed by translation of an open ferrule 138. The ferrule 138 has a threaded portion 141 threaded to internal cap threads 143 on the open cap 142 which is annularly snap-fit at 144 to allow annular rotation through the peripheral, snap-fit groove 117 in the housing wall 116.

Rotation of the cap 142 facilitated by finger grips 145 causes threaded drive translation leftwardly from the position shown in FIG. 8 to the position shown in FIG. 9 producing the longitudinal compression and induced radially inward squeezing of the compression flange portion 125 of the tubular diaphragm 120 to produce the secured gripping of the catheter portion C as well as the extruded seal engagement of the compression flange portion against the interior surface of the housing endwall 119. The longitudinal compression of the flange portion 125 also forces partial extrusion through the hole 101 in the seat 100 as shown in FIG. 9. The inserted catheter portion C is squeezed and supported by the compression of the flange 138. A stop portion 139 of the ferrule 138 travels through a keyway 147 within the cap 142 and impinges a stop surface 152 formed on the housing end 119. The seat 100 has a passageway slot 106 which provides fluid communication between the fluid pressure supply conduit 115 and the housing vent groove 111 extending longitudinally along the pressure chamber 130.

After compression operation on the stent, the ferrule 138 is unscrewed and backed off returning to the position in FIG. 8 to relieve the compression of the elastomeric spring-like flange portion 125 and to release the grip of the catheter, allowing withdrawal of the compressed stent.

The invention claimed is:

1. A method for uniformly compressing and conforming adhesion of a vascular stent upon an angioplasty balloon, comprising the steps of: providing a vascular stent and a deflated balloon, said deflated balloon having a surface; providing an elastic diaphragm within a housing, said elastic diaphragm and said housing forming a pressure chamber therebetween; dilating said elastic diaphragm; inserting said vascular stent and said deflated balloon into said dilated elastic diaphragm such that said vascular stent is positioned around said deflated balloon; and pressurizing said pressure chamber to compress said elastic diaphragm and to apply circumferentially uniform pressure onto said vascular stent to produce compression of the vascular stent into purchase onto the deflated balloon surface by transmitting fluid pressure around said elastic diaphragm, thereby engaging and compressing said vascular stent onto the deflated balloon surface.

2. A method according to claim 1, wherein said step of dilating said elastic diaphragm comprises at least partially evacuating fluid pressure from said pressure chamber.

3. A method according to claim 1, further including the step of providing said vascular stent on said deflated balloon prior to insertion into said dilated elastic diaphragm.

4. A method according to claim 1, wherein said step of pressurizing said pressure chamber comprises transmitting fluid pressure around said elastic diaphragm.

5. A method according to claim 1, wherein prior to said step of dilating said elastic diaphragm, said elastic diaphragm has a diameter which is slightly less than a diameter of said vascular stent when compressed onto the deflated balloon surface.

\* \* \* \* \*